United States Patent [19]

Teillaud et al.

[11] Patent Number: 5,499,967
[45] Date of Patent: Mar. 19, 1996

[54] TRANSDERMAL DRUG DELIVERY DEVICE WITH WAVESHAPE GENERATOR

[75] Inventors: Eric Teillaud, Talant; Bruno Bevan, Chevigny St Sauveur; Claude Mikler, Dijon, all of France; Paul Reilly, Hardwick, United Kingdom; Philippe Millot, Dijon, France

[73] Assignee: Societe anonyme dite: Laboratoires D'Hygiene Societe anonyme dite: et de Dietetique (L.H.D.), Paris, France

[21] Appl. No.: 181,078

[22] Filed: Jan. 13, 1994

Related U.S. Application Data

[63] Continuation-in-part of Ser. No. 16,269, Feb. 11, 1993, Pat. No. 5,426,387.

[30] Foreign Application Priority Data

Feb. 27, 1992 [FR] France ................... 92 02276

[51] Int. Cl.⁶ ........................................ A61N 1/30
[52] U.S. Cl. .................................. 604/20; 607/72
[58] Field of Search ............ 604/20–21; 607/72, 607/59; 328/14, 142; 377/56; 323/283

[56] References Cited

U.S. PATENT DOCUMENTS

| | | | |
|---|---|---|---|
| 3,970,919 | 7/1976 | Butcher. | |
| 4,019,510 | 4/1977 | Ellis | 604/20 |
| 4,141,359 | 2/1979 | Jacobsen et al. | 604/20 |
| 4,301,794 | 11/1981 | Tapper | 604/20 |
| 4,340,047 | 7/1982 | Tapper et al. | 604/20 |
| 4,406,658 | 9/1983 | Lattin et al. | 604/20 |
| 4,764,164 | 8/1988 | Sasaki | 604/20 |
| 4,895,153 | 1/1990 | Takeuchi et al. | 607/72 |
| 5,002,527 | 3/1991 | Reller et al. | 604/20 |
| 5,213,568 | 5/1993 | Lattin et al. | 604/20 |
| 5,246,418 | 9/1993 | Haynes et al. | 604/20 |

FOREIGN PATENT DOCUMENTS

| | | |
|---|---|---|
| 2603755 | 3/1988 | France. |
| 2656223 | 6/1991 | France. |
| 3334461 | 4/1985 | Germany. |
| 2239803 | 7/1991 | United Kingdom. |
| WO8808729 | 11/1988 | WIPO. |

OTHER PUBLICATIONS

'Study Of The Mechanisms Of Flux Enhancement Through Hairless Mouse Skin By Pulsed DC Iontophoresis', Pikal and Shah, Pharmaceutical Research, vol. 8, No. 3, 1991, pp. 365–369.

'Facilitated Transdermal Delivery Of Therapeutic Peptides And Proteins By Iontophoretic Delivery Devices', Chien et al, Journal of Controlled Release, 13 (1990), pp. 263–278.

*Primary Examiner*—C. Fred Rosenbaum
*Assistant Examiner*—Mark Bockelman
*Attorney, Agent, or Firm*—Stevens, Davis, Miller & Mosher

[57] ABSTRACT

The device comprises a switched-mode power supply (1) equipped with an electronic switching member ($T_1$), the closing of which controls the power supply to an inductor ($L_1$) which discharges, when the member reopens, into a capacitor ($C_1$) at the terminals of which the output voltage of the device appears, characterized in that it comprises (a) storage means for recording a sequence of image numbers of successive segments of the predetermined waveform, (b) a clocked digital counter (2) and (c) means (3) for successively loading this counter (2) with each of the numbers of this sequence considered as a bound of the count performed by the counter (2), the latter cyclically controlling the closing of the switching member ($T_1$) for a predetermined time interval, each time the count performed reaches the limit thus fixed.

6 Claims, 5 Drawing Sheets

TRANSDERMAL DRUG DELIVERY DEVICE WITH WAVESHAPE GENERATOR

This application is a continuation-in-part of U.S. patent application Ser. No. 08/016,269 filed Feb. 11, 1993, now U.S. Pat. No. 5,426,387.

The present invention relates to a device for generating an electrical voltage of predetermined waveform and, more particularly, to an apparatus for transdermally administering medicinal product equipped with such a device.

Apparatuses for administering medicinal products by iontophoresis have been provided which are designed for causing ionized molecules of an active principle, which hereinafter will be called "medicinal product" or "drug", to penetrate through the skin of a patient, the flow of the ionized molecules being forced by a potential difference set up between two adjacent areas of the patient's skin. By way of example of such apparatuses, mention may be made of those described in Documents WO-A-88/08729 and FR-A-2,656,223.

The quantity of medicinal products thus absorbed by the patient per unit of time is clearly dependent on the electrical current which is created by the applied potential difference and which traverses the patient's skin on passing from one area to the other. Studies have shown the benefit of an accurate control of the strength of this current, which can be set up or cut off for predetermined successive time periods, or amplitude modulated according to pulses of sinusoidal, triangular, sawtooth or square waveform, according to various programs for administering medicinal product which are adapted to particular treatments, to particular molecules, etc. Reference may be made in this regard to the article entitled "Study of the mechanisms of flux enhancement through hairless mouse skin by pulsed DC iontophoresis" by Pikal and Shah, published in the journal "Pharmaceutical Research", volume 8, No. 3, 1991, pages 365 to 369 and to the article entitled "Facilitated transdermal delivery of therapeutic peptides and proteins by iontophoretic delivery devices" by Chien and others, published in "Journal of Controlled Release", 13, 1990, pages 263 to 278. As is explained in these publications, the prolonged application of a DC voltage to the skin causes an electrochemical polarization of the latter especially because of a capacitive effect observed in the horny layer, this polarization causing a decrease in the electrical current associated with the iontophoretic transfer of the ionized molecules constituting the medicinal product, and therefore a reduction in the quantities of medicinal product which are administered per unit of time, with respect to the desired quantities. A known solution to this problem consists in using pulsed DC voltages providing times for depolarizing the horny layer.

For the iontophoretically assisted transdermic administration of medicinal products, it is currently sought to produce delivery apparatuses taking the form of lightweight compact bracelets which can be fixed without discomfort to the patient's arm, for several hours, for example. Such bracelets have to comprise a reserve of medicinal products to be administered and means for generating an electrical voltage suitable for iontophoretically assisting the migration of the ionized molecules, constituting the medicinal product, through the patient's skin. The reserve of medicinal products may be constituted by a hydrogel filled with the ionized form of the medicinal product and placed between the patient's skin and at least one of the two electrodes between which a voltage of predetermined waveform is applied. The means for generating this voltage should ideally, as has been seen above, be capable of delivering voltages of very varied waveform, frequency and amplitude, and in a programmable manner so that the apparatus can be used very flexibly. The electrical power supply to the apparatus must preferably be set up by batteries in order to ensure the autonomy of the patient, which necessitates taking into account the limited lifetime of these batteries and providing means for raising the voltage delivered by the batteries, the transdermic and iontophoretic administration of medicinal products currently requiring instantaneous voltages of 10 V or more. These constraints, combined with those of compactness and low weight, make the design of such apparatuses difficult.

In particular, in order to constitute waveform-programmable voltage generation means, it is possible to consider using a digital-to-analog converter, the digital input of which is supplied by a control device such as a microprocessor, the latter successively providing the converter with digital values reflecting the amplitude of successive segments of any voltage waveform. Unfortunately, taking into account the necessary high output voltage mentioned hereinabove, this solution leads to the use of a converter in a separate casing, which increases the cost and the bulk of the apparatus. Furthermore, a digital-to-analog converter is comparable to a class B amplifier, that is to say an amplifier acting over one half-period of the waveform only and therefore having an efficiency substantially less than 100%.

An object of the present invention is therefore to produce a device for generating an electrical voltage of predetermined waveform, which can be used in an apparatus for transdermally administering medicinal products, which does not have the drawbacks of the known solutions mentioned hereinabove, which is particularly lightweight, compact and supplied by electrical batteries so as to be autonomous and able to be worn by the patient, without discomfort, for long periods of time.

Another object of the present invention is to produce such a device, and such an apparatus allowing complete programming of the waveform of the applied voltage and of the program for delivering the medicinal product, so as to make the apparatus very flexible to use.

A further object of the present invention is to produce such a device and such an apparatus which allow the generation of AC waveform pulses, in order especially to ensure the migration of the medicinal product in the two successive directions of the current thus set up.

Still another object of the present invention is to produce such a device and such an apparatus which enable the applied current or voltage to be regulated so as to compensate for the time variations in the patient's resistance, as it is seen by the apparatus between two electrodes for applying the voltage which it develops.

These objects of the invention, as well as others which will appear on reading the description which follows, are achieved with a device for generating an electrical voltage of predetermined waveform, comprising a switched-mode power supply equipped with an electronic switching member, the closing of which controls the power supply to an inductor which discharges, when the member reopens, into a capacitor at the terminals of which the output voltage of the device appears. According to the invention, the latter comprises a) storage means for recording a sequence of numbers which are images of successive segments of the predetermined waveform, b) a clocked digital counter and c) means for successively loading this counter with each of the numbers of the sequence considered as bound of the count performed by the counter, the latter cyclically controlling the closing of the switching member for a predetermined time interval, each time the count performed reaches the bound thus fixed.

By virtue of the use according to the invention of a switched-mode power supply controlled by a counter, a compact, lightweight and autonomous device is obtained, making it very flexible to use in terms of available waveform.

According to a preferred embodiment of the device according to the invention, the counter is a down counter counting down from the loaded number and equipped with a zero-detection output controlling the closing of the switching member for the predetermined time interval, this member being constituted by a transistor, the zero-detection output of the counter being looped back to an enable input of the counter in order to trigger a new down-count from the number loaded.

According to an advantageous characteristic of the device according to the invention, the latter furthermore comprises means for stabilizing the current, which are interposed between the capacitor of the switched-mode power supply and an external load supplied by the voltage delivered by the device. This arrangement enables the current flowing into the patient to be made substantially independent of the resistance of the latter, which is important for controlling the quantity of medicinal product administered per unit of time.

Advantageously, the device furthermore comprises means for reversing the direction of flow of the current in an external load, these means being activated on detecting the loading into the counter of an image number of a zero crossing by the desired waveform of the output voltage from this device, this waveform being an alternating waveform having symmetrical half-waves, of which the image numbers of only one half-wave are loaded into the storage means.

According to another advantageous characteristic of the device according to the invention, the latter furthermore comprises means for regulating, in closed loop, the voltage or the strength of the output current of the device.

The invention thus makes it possible to constitute an apparatus for transdermally delivering medicinal products, of the type comprising at least two electrodes brought into contact with two adjacent areas of the skin of a patient, a reserve of a medicinal product having electrically transported molecules which is arranged against at least one of the electrodes in order to come into contact with the patient's skin, these electrodes being supplied by the output of the electrical-voltage generating device according to the present invention. Advantageously, a reserve of medicinal products is arranged against each of the two electrodes in order to permit a delivery of the medicinal product in the two directions of flow of the current between these electrodes.

BRIEF DESCRIPTION OF THE DRAWINGS

Other characteristics and advantages of the present invention will emerge on reading the description which follows and on examining the attached drawing in which.

DETAILED DESCRIPTION OF THE PREFERRED EMBODIMENT

Figure 1:
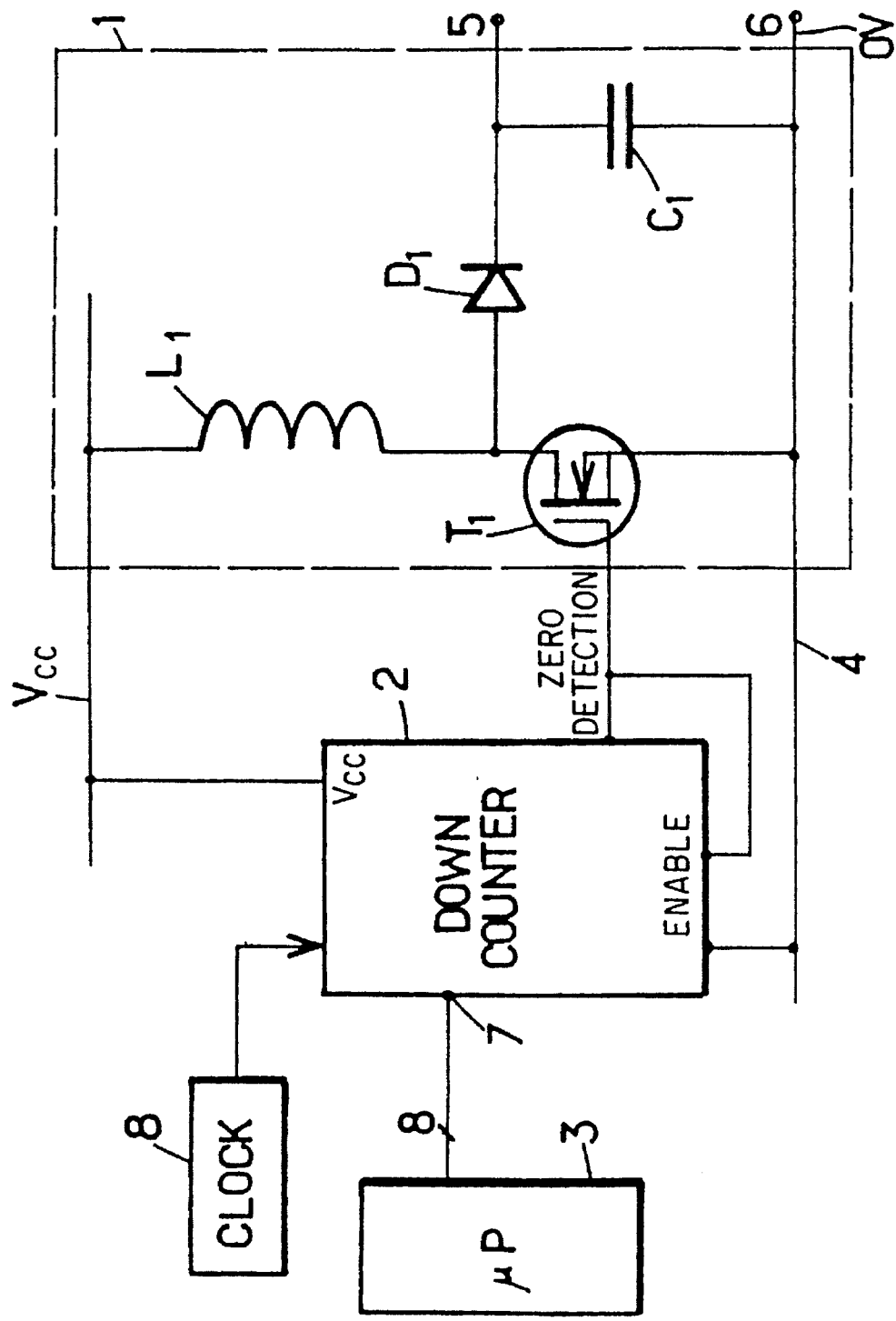
FIG. 1 shows diagrammatically the voltage-generating device according to the invention.

Referring to the diagram of FIG. 1, it appears that the device according to the invention essentially comprises a switched-mode power supply 1 controlled by a counter 2 which is itself connected to means for storing and loading numbers, which means are constituted by a microprocessor 3, for example. The switched-mode power supply is conventionally constituted by an inductor $L_1$ arranged in series with a transistor $T_1$ of the p-channel MOS type, between a reference voltage source $V_{cc}$ and an earth line 4. A diode $D_1$ is mounted, forward biased, between on the one hand, the point common to the inductor $L_1$ and the drain of the transistor $T_1$ and, on the other hand, a terminal of a capacitor $C_1$ which is arranged between the diode and the earth line 4. The operation of such a switched-mode power supply 1 is conventional. The current in the inductor $L_1$ increases each time the transistor $T_1$ is conducting, with a slope which is determined by the value of the inductance and that of the voltage $V_{cc}$. When $T_1$ stops conducting, the energy stored in the magnetic field of the inductor $L_1$ is transferred into the capacitor $C_1$ through the diode $D_1$. At each transfer, the voltage between the terminals 5 and 6 of the capacitor $C_1$ increases incrementally and can, in the absence of a load connected between the terminals 5 and 6, reach a very high voltage.

According to the present invention, the switched-mode power supply 1 is controlled by a "zero-detection" output of the counter 2, which can, for example, be an eight-stage synchronous down counter. Each time the counter passes through zero, a pulse of determined duration appears at this output and causes the transistor $T_1$ to conduct, which triggers the increase of the current in the inductor $L_1$.

The counter 2 is itself loaded with a number or "vector" defined over eight bits, for example. The vector is delivered on parallel data inputs 7 of the counter in order to load an upper bound of the down-count performed by the counter. Thus the time interval separating the appearance of two successive pulses at the "zero-detection" output depends on the value of this number or vector. By bringing these pulses closer together in time, the charging rate of the capacitor $C_1$ is accelerated, whereas, by moving them apart, this charging rate is decreased. It may be envisaged thus being able to give the voltage available between the terminals 5 and 6, which is delivered to a fixed external load (not shown), any form defined by a sequence of values of a "vector", which values are successively loaded into the counter in order to vary the time interval separating two consecutive pulses for causing the transistor $T_1$ to conduct.

The sequence of the values of the vector corresponding to a given waveform, sinusoidal, triangular, square or sawtooth for example, symmetrical or otherwise, thus constitutes a sequence of numbers, each of which is an "image" of one of the successive segments into which a waveform may be chopped up. This sequence of numbers is preserved in storage means which may, preferably but not exclusively, be internal to the microprocessor 3. The latter is duly programmed in order to set the rate of the delivery of these values to the counter, the latter constantly "revolving"

between the maximum value loaded and the value 0, the counting resuming immediately on each 0 crossing on account of the looping of the zero-detection output back to the "enable" input of the input 7. Conventionally, as shown, the counter is connected by its clock input 20 to a clock 8 and supplied between the voltage source V and the earth line 4.

Figure 4:
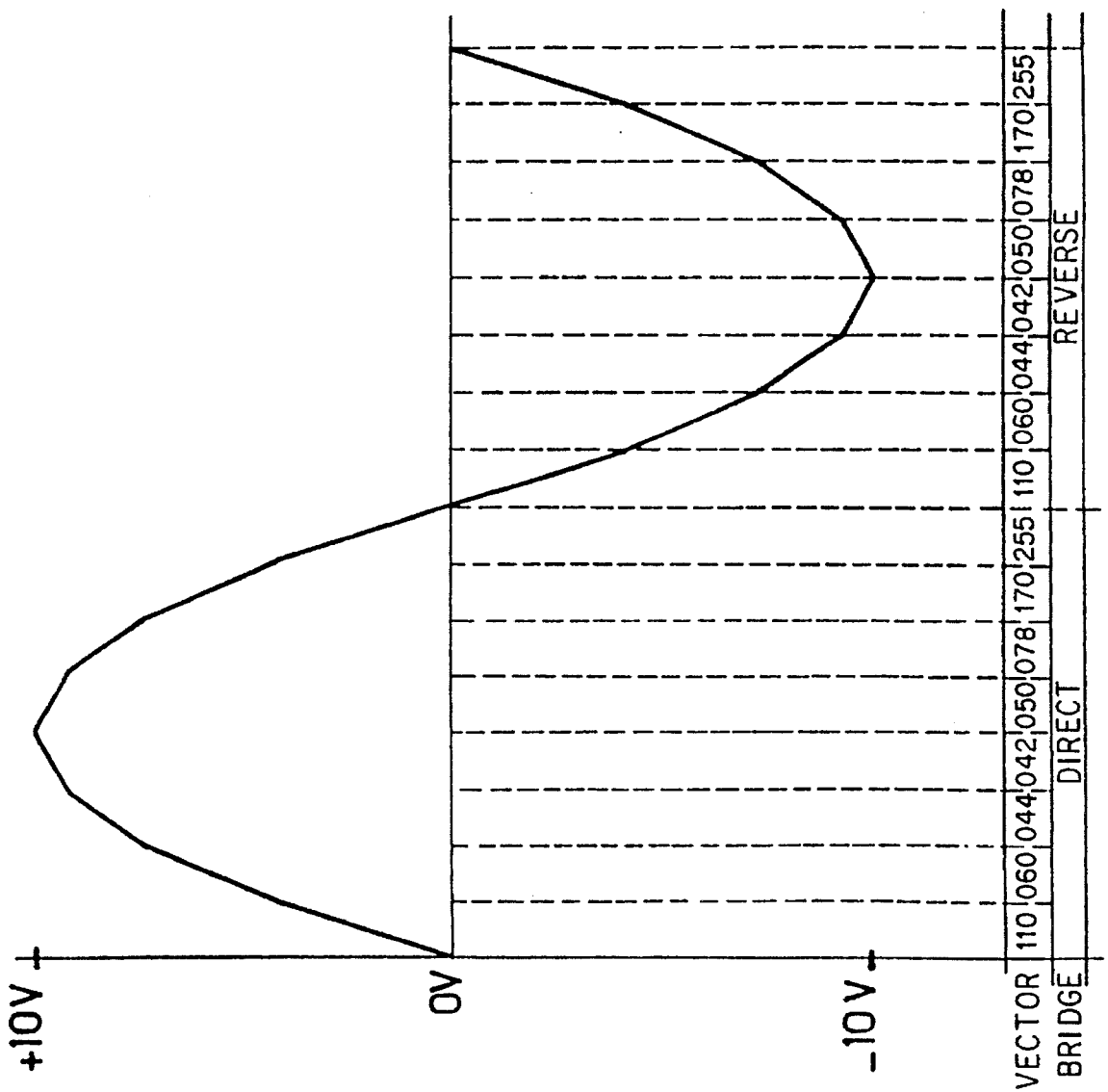
FIG. 4 explains, by way of example, the generation of a sinusoidal voltage by the device according to the invention; and, FIG. 5 shows a modification of the part of the device shown in FIG. 3.

By way of example, FIG. 4 shows the sequence of values of the vector which can be used for obtaining a sinusoidal waveform always assuming that the power supply is applied to a fixed external load. A high value of the vector (110, for example) has the effect of setting up a long counting period and, consequently, a low excitation frequency of the switched-mode power supply, which results in a low output voltage. A vector of lower value ensures a shorter counting period, a higher excitation frequency of the switched-mode power supply and therefore an increased output voltage. By rapidly varying the vector cyclically, it is possible to generate any waveform including constant levels, triangular or rectangular pulses, sawteeth and sinusoids. For the generation of a symmetrical and sinusoidal alternating waveform, such as that shown in FIG. 4, it is possible to generate the second half-wave of the waveform by simply reversing the direction of passage of the current in the external load, which reversal is obtained by means which will be described below, the sequence of the values of the vector (110, 060, 044, etc.) for only a half-wave then being put into store.

According to an advantageous characteristic of the device according to the invention, the latter comprises particularly simple means for varying the frequency of the waveform set up; it suffices to regulate the rate at which the microprocessor loads the counter with the successive values of the vector.

It will be noticed that the duration of the pulse for causing the transistor $T_1$ to conduct is equal to the period of the signal delivered by the clock 8 which sets the rate of the counter 2, this duration thus being fixed very accurately. The pulse repetition period is variable, equal to the duration of the base pulse multiplied by the value of the vector, increased by one unit. It will be further noticed that the switched-mode power supply 1 is of the type which makes it possible to deliver an output voltage greater than the input voltage. This is necessary in the application, described below, of the invention to an iontophoretic apparatus for transdermally delivering medicinal products, which has to be powered by small batteries in order to be able to be worn by a patient, without discomfort. In such an application, it is necessary to be able to reach, as has been seen above, voltages greater than 10 V with two 3 V batteries for example, and it is therefore necessary to use a voltage-raising switched-mode power supply.

Figure 2:
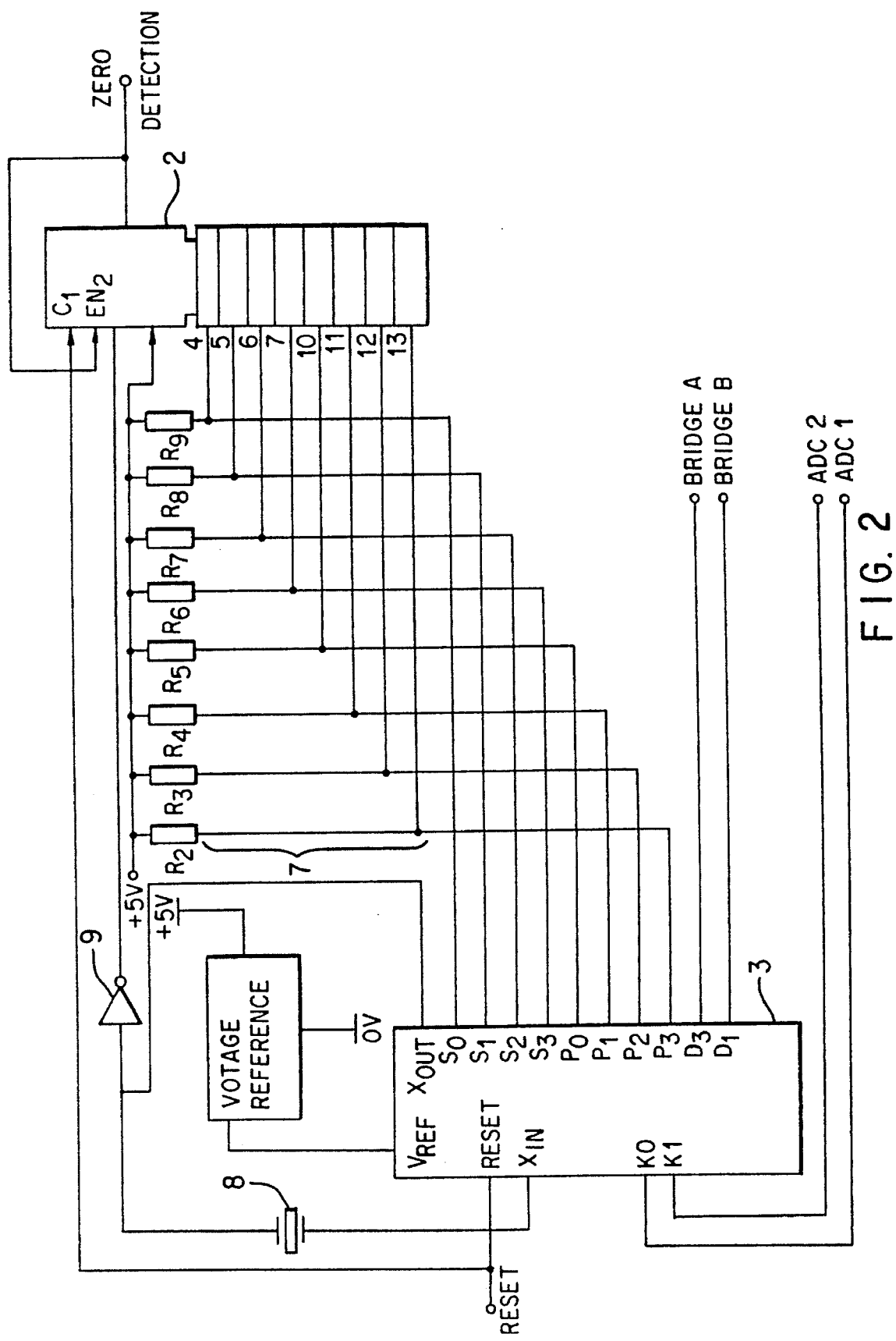
FIG. 2 is a diagram of a particular embodiment of the connections set up between a microprocessor and a counter forming part of the device according to the invention.

Reference is now made to FIG. 2 of the attached drawing which shows in more detail the means used for loading a vector value into the counter 2, from the microprocessor 3. By way of non-limiting example, the counter 2 is constituted by an eight-stage synchronous down counter having the reference 74HC40103 in the catalogues of the SGS Thomson Company, while the microprocessor used is that having the reference M50927E in the catalogues of the MITSUBISHI Company.

Each of the eight lines of the parallel input 7 of the counter has been shown, each loaded via a resistor ($R_2$ to $R_9$), as is conventional. The outputs $S_0$ to $S_3$ and $P_0$ to $P_3$ of the microprocessor supply these lines, which are connected to the pins 4–7 and, 10–13 of the counter. A crystal clock 8 supplies a clock signal to the clock input 20 of the counter via an inverter 9, and the microprocessor directly on its clock input XIN. The resetting of the microprocessor and of the counter through its reset input $C_1$ can be controlled by a RESET terminal. A reference voltage source 10 supplies the microprocessor. As concerns counter 2, the "zero-detection" output is looped back to an enable input EN2, as in the diagram of FIG. 1.

FIG. 2 further shows two lines, "bridge A" "bridge B", respectively connected to outputs $D_3$ and $D_4$ of the microprocessor and two lines, ADC1 and ADC2, connected to inputs K0 and K1 of the microprocessor which are equipped with built-in analog-to-digital converters. The roles of these four lines will be explained in conjunction with the examination which will follow of the diagram shown in FIG. 3.

In this figure, three units have been enclosed by broken lines, respectively corresponding to the switched-mode power supply 1 described hereinabove, to current-stabilizing means 11 and to means 12 for reversing the direction of current in the external load. The base of the transistor T1 of the switched-mode power supply 1 is connected to the "zero-detection" output of the counter 2 via an inverter 17.

The two aforementioned lines ADC1 and ADC2 form part of means for the closed-loop control of the current or the voltage applied to this external load which is connected between electrodes 13 and 14 forming, in a particular application of the invention, part of an iontophoretic apparatus for transdermally administering medicinal products.

Such an apparatus is constituted by arranging, in a casing capable of being held by a bracelet on a limb of a patient, a device for generating an electrical voltage according to the present invention and one or more small-scale electrical batteries such as lithium batteries for the power supply to the device. The electrodes 13, 14 are connected, possibly in a separable manner, to the output terminal of the circuit of FIG. 3. At least one of these electrodes is lined with a reserve of the medicinal product to be administered, such as a hydrogel loaded with the ionized form of this medicinal product, this hydrogel being applied against the skin of a patient to be treated. The two electrodes then face two adjacent areas of the patient's skin and the voltage developed by the device according to the invention causes, when it is suitably oriented, a migration of the ionized molecules of the medicinal product through the patient's skin, migration forced by the electric field set up between the two electrodes, which extends under the patient's skin.

Up to now, the invention has been described in its application to an iontophoretic migration of medicinal products. Of course, it is clear that the invention extends to any transdermal administration of medicinal products transported electrically through the skin, whether by iontophoresis or by electroosmosis, for example, or by a combination of both these effects.

Figure 3:
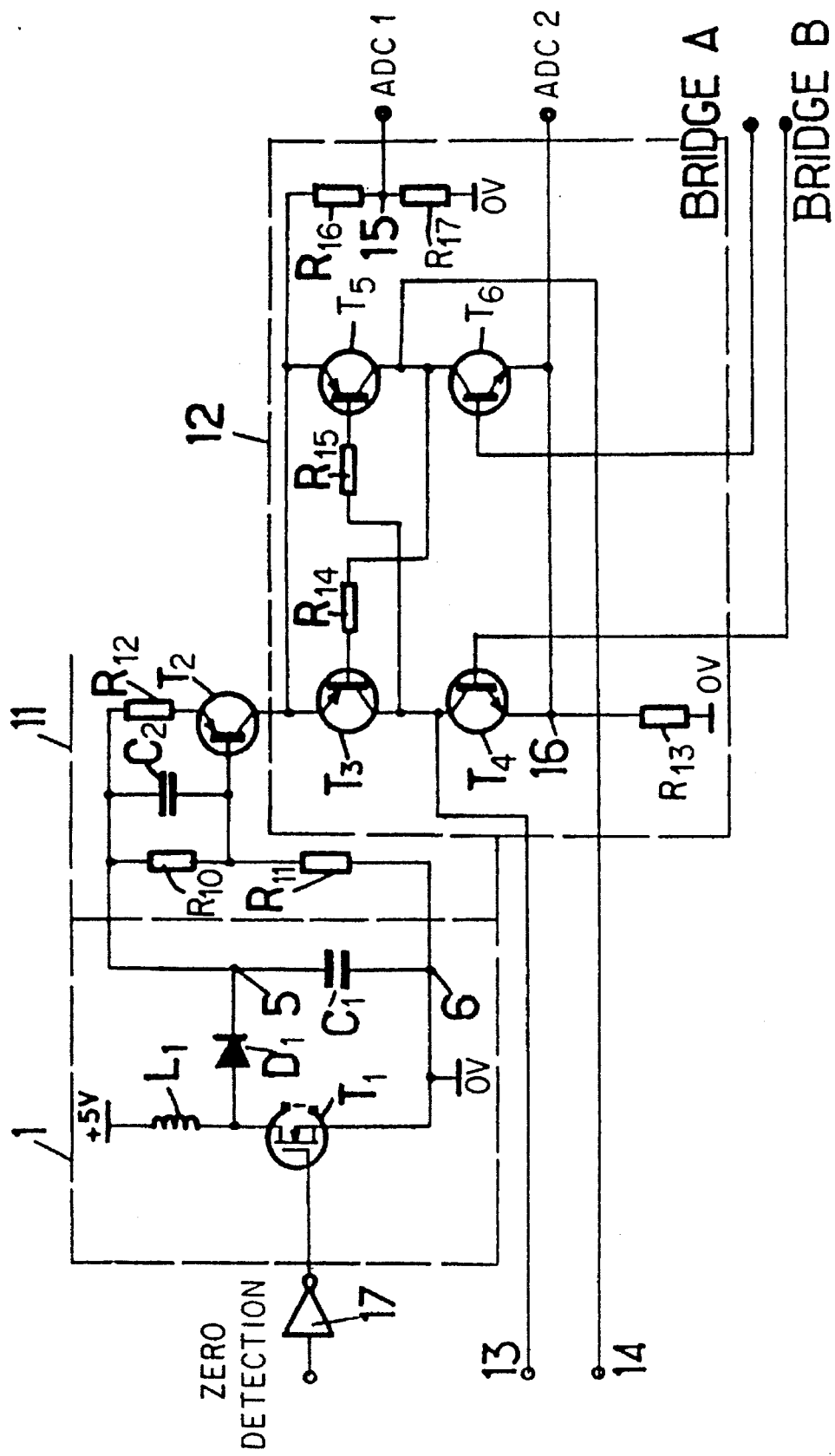
FIG. 3 shows, in more detail, that part of the device according to the invention which is controlled by the output of the zero detector of the counter of FIG. 2 in order to supply the electrodes of an iontophoretic apparatus for transdermally administering medicinal products according to the invention.

The circuit of FIG. 3 is designed to carry out various functions particularly useful in the application described hereinabove.

Thus, the circuit comprises the means 11 for stabilizing the current delivered to the patient, these means comprising a transistor $T_2$, the base of which is connected to the mid-point of a resistor bridge $R_{10}$, $R_{11}$ connected to the terminals of the capacitor $C_1$, a resistor $R_{12}$ arranged on the emitter of the transistor $T_2$ limiting the current delivered by this transistor to the external load. Indeed, the base of the transistor $T_2$ is held at a voltage proportional to that of the terminal 5 of the capacitor $C_1$ by virtue of the bridge $R_{10}$, $R_{11}$. The voltage at the terminals of the emitter resistor $R_{12}$ is then proportional to that prevailing at the terminal 5 less a constant value determined by the emitter/base voltage of the transistor $T_2$. The voltage at the terminals of the emitter resistor $R_{12}$ in turn determines the emitter current and, thereby, the current in the collector of this transistor. This current is substantially independent of the collector resistance which is partially determined by that of the patient, as "seen" between the electrodes 13 and 14. The stabilization means described make the strength of the current flowing into the patient (and therefore the flow rate of medicinal product) substantially independent of the patient's resistance, which may vary from one subject to another. The presence will also be noted of a capacitor $C_1$ connected in parallel with the resistor $R_{10}$, the combination constituting a filter which smooths the output of the switched-mode power supply 1.

As has been seen hereinabove, the device according to the invention also comprises means 12 for reversing the direction of the current in the external load, between the two electrodes 13, 14, which enables alternating waveforms to be generated consisting of two symmetrical half-waves with the aid of the store of vector values corresponding to one half-wave only. FIG. 3 shows that these means 12 are interposed between the transistor $T_2$ and the electrodes 13, 14. The means 12 are constituted by a bridge of four transistors $T_3$, $T_4$, $T_5$, $T_6$ arranged so as to supply the external load by a diagonal, the bases of two transistors $T_3$, $T_5$ of a first (pnp) type being coupled to the collector of the other two transistors $T_4$, $T_6$ of a second (npn) type, the conduction states of which are reversed on detection, by the means for loading a number corresponding to the zero crossing of the waveform.

Of course, the transistor bridge could also be used for generating waveforms having asymmetrical half-cycles, the entire waveform then having to be stored.

The bases of the transistors $T_3$, $T_5$ are respectively connected to the collectors of the transistors $T_4$, $T_6$ via resistors $R_{14}$, $R_{15}$ respectively. The bases of the transistors $T_4$, $T_6$ are controlled by signals on lines "bridge B", "bridge A" respectively transmitted by the microprocessor 3 (see FIG. 2). The electrodes 13, 14 are connected to the collectors of the transistors $T_3$ and $T_5$, along a "diagonal" of the bridge. In the embodiment shown, the storage means and the means for loading the values of the vector are combined in the microprocessor and the latter is furthermore equipped with means for detecting the value of the vector which corresponds to the zero crossing by the waveform, these means triggering the transmission of the "bridge A" and "bridge B" signals. It is clear that, when the transistor $T_4$ is made conducting by the transmission of a bridge B signal, the conduction of the transistor $T_4$ triggers that of $T_5$, the current leaving the collector of the transistor $T_2$ passing into the patient from the electrode 14 towards the electrode 13. The current passes in the other direction when the microprocessor triggers the conduction of the transistors $T_3$ and $T_6$.

Under certain circumstances it has been noted that the above described correct operation of the means 12 for reversing the direction of the current in the external load is prevented by a so-called "battery-effect" developed between electrodes 13,14 when in contact with the skin of a patient. As a matter of fact, because of an ion concentration gradient at the interface between the skin and the ion-loaded hydrogel layer contacting said skin, and also because of the adjacent metal electrode, an electromotive force is generated between electrodes 13,14. The voltage available due to this "battery effect" can reach a substantial level, capable of preventing the control signals on terminals "bridge A", "bridge B" to trigger transistors $T_3$, $T_5$. This phenomenon was observed in particular with a pulsed current of about 1 mA, operated at 1 kHz.

Figure 5:
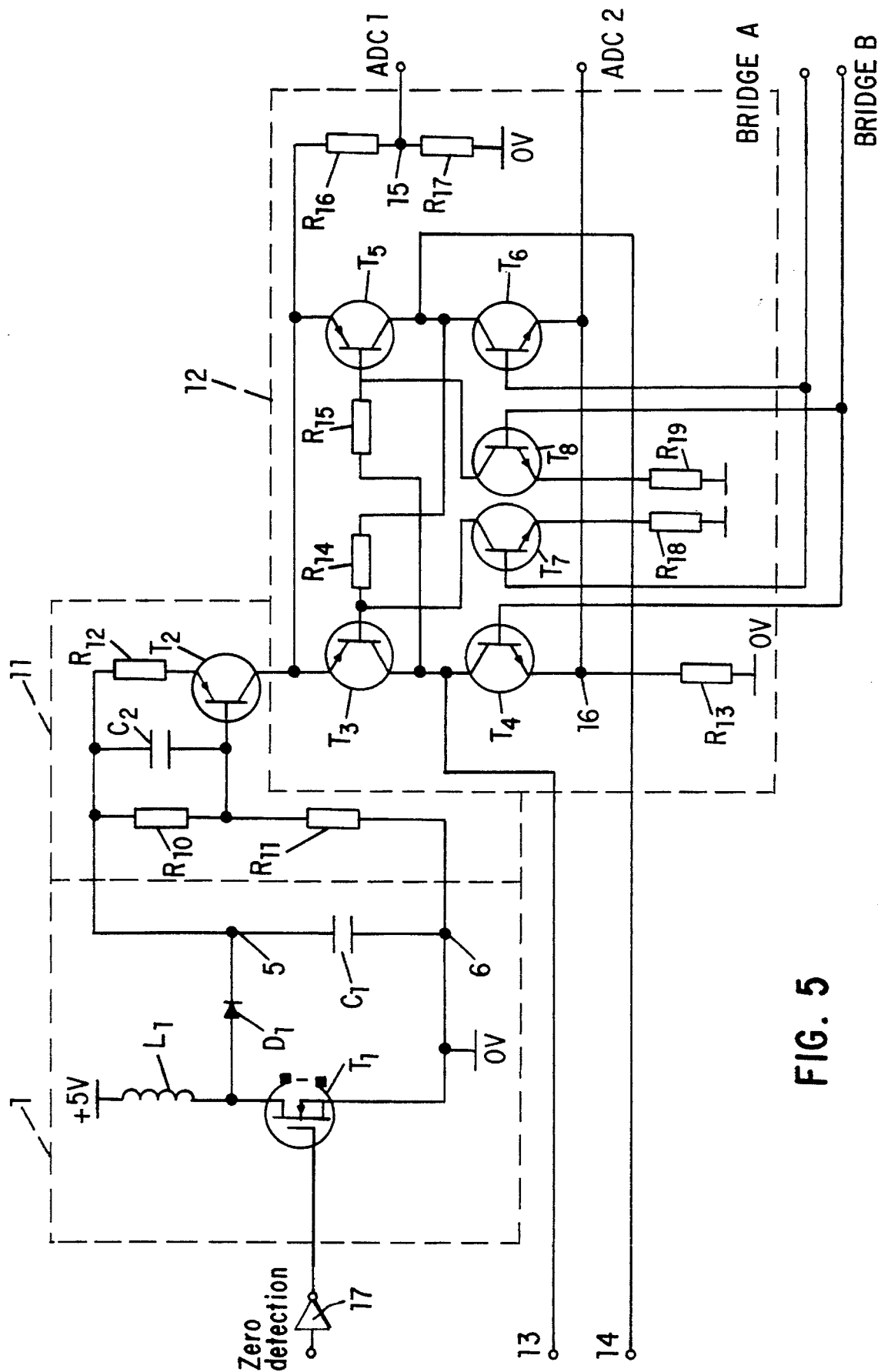

According to the present invention, this deficiency can be eliminated by providing the bridge (as shown in FIG. 5) with two further transistors $T_7$, $T_8$, of the NPN type, the collector-emitter circuits of which are connected between the bases of transistors $T_3$, $T_5$ and resistors $R_{18}$, $R_{19}$, respectively, the other terminals of which resistors are grounded. The bases of transistors $T_7$, $T_8$ are controlled by the signals on terminals "bridge A" "bridge B", respectively Thus, when a "high" control signal on the BRIDGE A terminal makes transistor $T_6$ conductive, transistor $T_7$ is also made conductive so as to connect the base of transistor $T_3$ to ground. PNP transistor $T_3$ is thus made conductive to allow current to flow through electrode 13, then through electrode 14 and transistor $T_6$, down to the ground through resistor $R_{13}$. Grounding the base of transistor $R_3$ through transistor $T_7$ prevents, according to the present invention, said transistor $T_7$ from remaining blocked because of the above mentioned emf existing between electrode 13 and 14. Reversing the flow of current in the load by means of an appropriate control of terminal BRIDGE B will lead to a similar operation of transistor $T_4$ and $T_6$.

In the application of such a device to an iontophoretic migration of medicinal products, the dual-direction migration which it is thus possible to obtain is advantageous when two electrodes are used, each associated with a reserve of medicinal product. Compared to an apparatus comprising a single reserve associated with one of the electrodes only, it is possible to double the flow rate of medicinal product. For a same flow rate, the latter is set up from two separate areas of the patient's skin, which makes it possible to reduce the latter's irritation due to the transdermal effect.

According to another advantageous characteristic of the device according to the invention, the latter may be equipped with means making it possible to provide a closed-loop regulation of the voltage or of the strength of the currents which are applied to the patient between the electrodes 13 and 14. The patient's resistance may, in fact, vary over time, during the treatment, in particular on account of the polarization of the horny layer of the skin, despite the depolarizing effect of the application of pulsed voltages which limit this polarization. This resistance variation may lead to variations in the voltage or current applied to the patient, outside predetermined regions beyond which the treatment is not performed correctly.

According to the invention, such resistance variations are detected with the aid of voltages $V_1$, $V_2$, picked up upstream and downstream of the transistor bridge $T_3$, $T_4$, $T_5$, $T_6$, at the points 15 and 16 respectively, via the lines ADC1 and ADC2, respectively.

The voltage $V_1$ picked up at the mid point 15 of a divider bridge $R_{16}$, $R_{17}$ connected between the collector of the transistor $T_2$ and earth is supplied to the input K0 of the microprocessor, whereas the voltage $V_2$ at the emitters of the transistors $T_4$, $T_6$ at point 16 is delivered to the input K1 of the microprocessor, which converts them into digital values.

The voltage $V_1$ enables the microprocessor to calculate the voltage on the input electrode of the current passing into the patient, whereas the voltage $V_2$ applied to the resistor $R_{13}$ placed between the emitters of the transistors $T_4$, $T_6$ and earth enables the current $i=V_2/R_{14}$ passing into the patient to be calculated. The microprocessor then calculates the patient's resistance R:

$$R=(kV_1-V_2)/i$$

where k is a constant determined by resistors $R_{16}$ and $R_{17}$.

From the variations in the patient's resistance which may thus be observed, the microprocessor carries out closed-loop control of the voltage or current applied to the patient by increasing or by decreasing the value of the vector which is provided to the counter so as thus to keep the desired voltage or current strength value. The feedback thus obtained also makes it possible to enable a halt or a modification to the stimulation of the patient to be ordered in the event of excessive or insufficient voltage, intensity or resistance, measured on the patient.

An iontophoretic apparatus for transdermally administering medicinal product has been constructed comprising a voltage-generating device in accordance with the present invention. Powered by two lithium batteries of the 2430 type, the apparatus makes it possible to deliver to the patient a current which can be regulated between 0 and 1 mA, continuously or according to any waveform pulses, possibly bipolar and having a frequency up to 80 Hz for a sinusoidal or triangular waveform and up to 2 kHz for square waveforms, the current obtained being accurate to better than 0.05 mA, for skin resistances ranging up to 20 k$\Omega$. It is possible for these results to be obtained by virtue of the characteristics and advantages of the present invention explained hereinabove and especially by virtue of the technique for loading a sequence of values of the "vector" into the counter which enables any waveform to be configured very flexibly. The closed-loop regulation using software stored into the microprocessor and the accurate measurement of the patient's resistance enable the current passing into the patient to be regulated very accurately, which compensates for the possible losses in the circuit. The use of a voltage-raising switched-mode power supply, controlled by a counter, enables an accurate, small-scale voltage source to be used. The use according to the invention of a bipolar waveform, in combination with two electrodes each lined with a hydrogel filled with medicinal products to be delivered to the patient, makes it possible to ensure this delivery in both directions of flow of the current, through two different areas of the patient's skin, which technique increases the tolerance of the patient to the iontophoretic current.

Of course the invention is not limited to the embodiment described and shown, which has been given by way of example only. Thus it is possible to replace the down counter used by an up counter, by means of adaptations which immediately spring to mind to the person skilled in the art.

More generally, the invention is applicable to apparatuses for transdermally delivering medicinal products, relying on phenomena other than iontophoresis, for example electroosmosis. Furthermore, the device for generating an electrical voltage according to the invention may also be incorporated into an apparatus for electrically stimulating the skin or organs such as nerves or muscles for therapeutic purposes such as, for example, the treatment of pain by transcutaneous neurostimulation or the activation of healing processes by stimulation of the injured skin, or even the muscular training or reeducation by transcutaneous electrostimulation of muscles.

We claim:

1. Apparatus for transdermally and iontophoretically delivering medicinal products comprising at least first and second electrodes designed to be put in contact with two adjacent areas of the skin of a patient, a reservoir of a medicinal product having electrically transportable molecules being arranged against at least the first of the electrodes in order to come into contact with the patient's skin, wherein the electrodes are supplied by a device for generating an electrical voltage of predetermined waveform, comprising a switched-mode power supply having an inductor serially connected to an electronic switching member, the closing of which controls the power supply of the inductor which discharges, when the member reopens, into a capacitor which is connected in parallel with the electronic switching member, the capacitor having terminals which are electrically connected to the electrodes, said device further comprising (a) storage means for recording a sequence of numbers which are images of successive segments of the predetermined waveform, (b) a clocked digital counter, (c) means for successively loading the counter with each of the numbers of the sequence considered as a bound of the count performed by the counter, and (d) means for reinitializing the counter each time the bound is reached, thereby cyclically controlling the closing of the switching member for a fixed time interval, each time the count performed reaches the bound fixed by the means for successively loading.

2. Apparatus according to claim 1, further comprising means for reversing the direction of flow of an output current supplied by the device to the electrodes, the means for reversing being actuated on detecting the loading into the counter of an image number of a zero crossing by the desired waveform, and a second reservoir of medicinal products being arranged against the second electrode.

3. Apparatus according to claim 2, wherein said reversing means comprise a bridge of four bridge transistors arranged so as to supply an external load by a diagonal, the bases of two bridge transistors of a first type being coupled to the collectors of the other two bridge transistors of a second type, the conduction states of which are reversed on detecting, by the loading means, a number corresponding to the zero crossing by the waveform.

4. Apparatus according to claim 3, wherein the bases of two of said bridge transistors of the same type are connected to ground through respective further transistors of the opposite type, each of said further transistors being switched on/off in synchronism with a bridge transistor of a common diagonal of the bridge.

5. Apparatus according to claim 1, further comprising means for closed-loop regulation of the voltage or the strength of the output current of the device, said means for closed-loop regulation comprising means for measuring the voltage and the current flowing into the patient between the first and second electrodes and for calculating the patient's resistance, seen between the first and second electrodes, and means for correcting the numbers successively loaded into the counter in order to compensate for the influence of a variation in this resistance on the voltage or the current flowing into the patient.

6. Apparatus according to claim 5, wherein the calculating and correcting means are incorporated into the microprocessor.

* * * * *